United States Patent [19]

Bailey

[11] 4,000,160
[45] Dec. 28, 1976

[54] PYRROLYL OXYPHENYL KETONES
[75] Inventor: Denis M. Bailey, East Greenbush, N.Y.
[73] Assignee: Sterling Drug Inc., New York, N.Y.
[22] Filed: Apr. 14, 1975
[21] Appl. No.: 567,592

Related U.S. Application Data

[63] Continuation-in-part of Ser. No. 350,103, April 11, 1973, abandoned.
[52] U.S. Cl. .................. 260/326.5 J; 260/326.43; 260/326.5 R; 424/274
[51] Int. Cl.² .................................... C07D 207/32
[58] Field of Search ........................... 260/326.5 J

[56] References Cited
OTHER PUBLICATIONS

Birchall et al., Tetrahedron Letters, No. 56, pp. 4879–4882 (1970).
Takeda, J. Am. Chem. Soc. vol. 80, pp. 4749–4750 (1958).
Bailey et al., J. Chem. Soc. D, 1969, (21), (Chem. Common), p. 1284 (1969).
Bailey et al., Can. J. Chem. 48, pp. 2257–2259 (1970).

Primary Examiner—Nicholas S. Rizzo
Assistant Examiner—Diana G. Rivers
Attorney, Agent, or Firm—William G. Webb; B. W. Wyatt

[57] ABSTRACT 4,5-Dihalopyrrol-2-yl oxyphenyl ketones, prepared either by Friedel-Crafts condensation of a 4,5-dihalopyrrole-2-carboxylic acid halide with an appropriate hydroxy or lower-alkoxy-substituted benzene or by condensation of a hydroxy or lower-alkoxy-substituted benzaldehyde with pyrrole in the presence of sodium hydride followed by halogenation, with elemental chlorine or bromine, of the resulting pyrrol-2-yl oxyphenyl ketone, useful as antibacterial and antifungal agents.

12 Claims, No Drawings

PYRROLYL OXYPHENYL KETONES

RELATED APPLICATIONS

This is a continuation-in-part of my prior, copending application Ser. No. 350,103, filed Apr. 11, 1973, now abandoned.

BACKGROUND OF THE INVENTION a. Field of the Invention

This invention relates to 4,5-dihalopyrrol-2-yl oxyphenyl ketones useful as antibacterial and antifungal agents.

b. Description of the Prior Art

The antibiotic, 4,5-dichloropyrrol-2-yl 2,6-dihydroxyphenyl ketone known as pyoluteorin, is known [Takeda, J. Am. Chem. Soc. 80, 4749–4750 (1958)]. It has now been found that certain analogs of pyoluteorin differing therefrom either in havng bromine in place of chlorine on the pyrrole ring, or in the number or position of the phenolic hyroxyl groups, or in having one or more methoxy groups in place of hydroxyl on the phenyl ring have superior in vitro activity against certain fungi in comparison with pyoluterorin, and certain specific analogs have superior in vitro activity against certain bacterial strains.

SUMMARY OF THE INVENTION

This invention relates in a composition of matter aspect to 4,5-di-X-pyrrl-2-yl 2-$R_1$-3-$R_2$-4-$R_4$-phenyl ketones, where X is chlorine or bromine and either one or two of $R_1$, $R_2$, $R_3$ and $R_4$ are hydroxy or lower-alkoxy, the others being hydrogen, which are useful as antibacterial and antifungal agents.

DETAILED DESCRIPTION INCLUSIVE OF THE PREFERRED EMBODIMENTS

More specifically, this invention relates to 4,5-dihalopyrrol-2-yl oxyphenyl ketones having the formula:

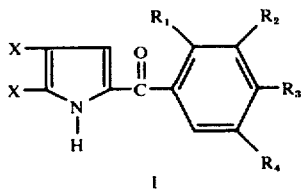

I wherein X is chlorine or bromine, both values of X being identical; one of $R_1$, $R_2$, $R_3$ and $R_4$ is hydroxy or lower-alkoxy, the others being hydrogen; or two of $R_1$, $R_2$, $R_3$ and $R_4$ are either both hydroxy or both lower-alkoxy, the others being hydrogen.

As used herein, the term lower-alkoxy means saturated, monovalent, aliphatic radicals, including straight or branched-chain radicals, of from one to four carbon atoms, as illustrated by methoxy, ethoxy, propoxy, isopropoxy, butoxy, sec.-butoxy, isobutoxy, t-butoxy, and the like.

Preferred compounds within the ambit of formula I as defined above are those having the formula:

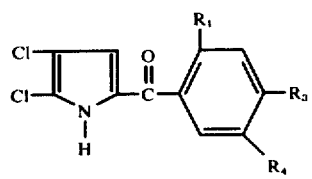

wherein two of $R_1$, $R_3$ and $R_4$ are either both hydroxy or both methoxy, the other being hydrogen.

Also preferred are compounds of formula I wherein (A) X is chlorine and either two of $R_1$, $R_2$, $R_3$ and $R_4$ are methoxy, the others being hydrogen or $R_1$ and $R_3$ are each hydroxy and $R_2$ and $R_4$ are hydrogen and (B) X is bromine and either $R_1$ and $R_4$ are each hydroxy and $R_2$ and $R_3$ are hydrogen or $R_2$ is methoxy and $R_1$, $R_3$ and $R_4$ are each hydrogen.

Other preferred compounds within the ambit of formula I are those having the formula:

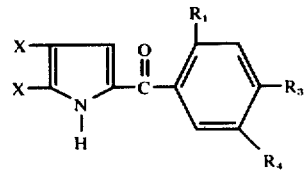

wherein either X is chlorine or bromine; $R_1$ and $R_4$ are each hydroxy; and $R_3$ is hydrogen or X is chlorine; $R_3$ is methoxy; and $R_1$ and $R_4$ are each hydrogen.

The compounds of formula I are prepared by a Friedel-Crafts condensation between a 4,5-dihalopyrrole-2-carboxylic acid halide and an appropriate hydroxy or lower-alkoxy-substituted benene, as represented by the following reaction:

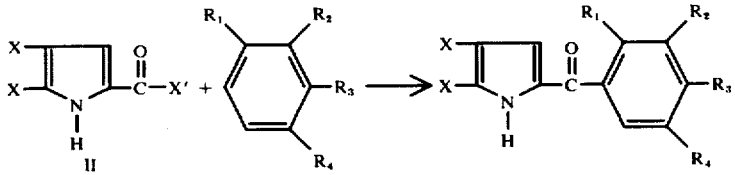

wherein X, $R_1$, $R_2$, $R_3$ and $R_4$ have the meanings given above, and X' represents halogen. The reaction is carried out in the presence of a Lewis acid catalyst, for example, stannic chloride or ferric chloride, at a temperature in the range from about 0° C. to about 20° C., and in an organic solvent inert under the conditions of the reaction, for example benzene, toluene or xylene. A preferred catalyst is stannic chloride, and a preferred solvent is benzene.

Alternatively, the compounds of formula I where one or two of $R_1$, $R_2$, $R_3$ and $R_4$ are lower-alkoxy are prepared by a sequence of reactions involving condensation of one molar equivalent of pyrrole with one molar equivalent of an appropriate lower-alkoxy-substituted-benzaldehyde in the presence of one molar equivalent of sodium hydride. The resulting alkoxyphenyl pyrrol-2-yl carbinol, which is not isolated, is then oxidized to the corresponding ketone by further reaction of the carbinol, in a Meerwin-Pondorf-Verley-type oxidation/reduction reaction, with a second molar equivalent each of sodium hydride and lower-alkoxy-substituted-benzaldehyde. The resulting pyrrol-2-yl lower-alkoxyphenyl ketones are then halogenated, with elemental chlorine or bromine, as described hereinafter. The compounds of formula I where one or two of $R_1$, $R_2$, $R_3$ and $R_4$ are hydroxy are prepared from the corresponding alkoxy-substituted compounds so-produced by cleavage of the alkoxy groups as described hereinafter. The overall method is represented by the following reaction sequence:

1976, and as disclosed in that application, are prepared by alkaline saponification of the corresponding 4,5-dihalopyrrol-2-yl trihalomethyl ketones, which are also disclosed in said copending application Ser. No. 349,973, by warming an aqueous mixture of the ketone and aqueous alkali followed by reaction of the resulting 4,5-dihalopyrrole-2-carboxylic acid with a thionyl halide.

The 4,5-dihalopyrrol-2-yl trihalomethyl ketones re-

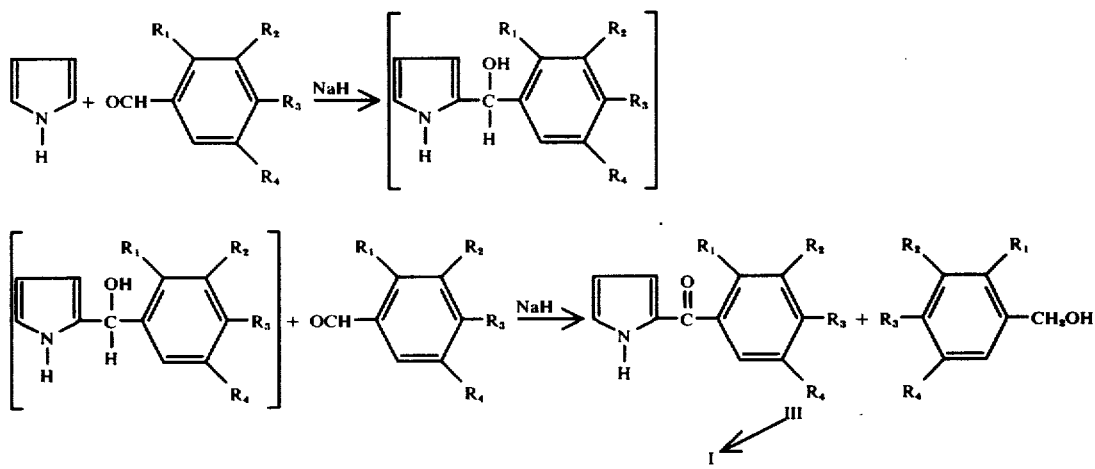

wherein X, $R_1$, $R_2$, $R_3$ and $R_4$ have the meanings given above. As indicated, in the initial step involving condensation of pyrrole with an appropriate lower-alkoxy-substituted-benzaldehyde, one mole of the aldehyde condenses with one mole of pyrrole, while the other mole of aldehyde is reduced, in a second step, to the corresponding lower-alkoxy-substituted-benzyl alcohol at the expense of the pyrrole/aldehyde carbinol condensation product. The reaction is carried out at a temperature from about 0° C. to about 50° C. in a mixed solvent of dimethylformamide and another organic solvent inert under the conditions of the reaction, for example benzene, toluene or xylene.

The halogenation of the compounds of formula III is carried out with elemental chlorine or bromine at a temperature in the range from about 0° C. to about 20° C., and in an organic solvent inert under the conditions of the reaction, for example, glacial acetic acid, chloroform, carbon tetrachloride, methylene dichloride, ethylene dichloride, and the like.

The above-described procedures are advantageously used for the preparation of the compounds of formula I wherein $R_1$, $R_2$, $R_3$ and $R_4$ represent one or two lower-alkoxy groups, while the compounds wherein $R_1$, $R_2$, $R_3$ and $R_4$ are one or two hydroxy groups are advantageously prepared from the corresponding lower-alkoxy compounds by cleavage of the latter with a strong Lewis acid, such as aluminum chloride or aluminum bromide. The reaction is carried out in an organic solvent inert under the conditions of the reaction, for example benzene, toluene, xylene, methylene dichloride, ethylene dichloride, and the like, and at a temperature in the range from 0° C. to about 30° C.

The 4,5-dihalopyrrole-2-carboxylic acid halides of formula II required as intermediates in the above-described Friedel-Crafts condensation are described in my copending application Ser. No. 349,973, filed Apr. 11, 1973 now U.S. Pat. 3,963,480, patented June 15, quired as intermediates for the preparation of the 4,5-dihalopyrrole-2-carboxylic acids are, in turn, prepared by reaction of pyrrole either with a trihaloacetyl halide or with a trihaloacetic anhydride, followed by halogenation of the resulting pyrrol-2-yl trihalomethyl ketone with elemental chlorine or bromine as described above. The reaction of pyrrole with the trihaloacetyl halide or the trihaloacetic anhydride takes place readily at room temperature by direct interaction of the two reactants in an aprotic organic solvent, for example diethyl ether, dioxane or tetrahydrofuran.

The compounds of formula I have been found to possess antibacterial activity. The antibacterial activity was determined using a modification of the Autotiter method described by Goss et al., Applied Microbiology, 16 (No. 9), 1414–1416 (1968) in which a 1000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semisynthetic medium (glucose). After this operation, 0.05 ml. of inoculated semisynthetic medium is added automatically to each cup. The overall operation results in final drug concentrations ranging from 500 to 0.06 mcg./ml. in twofold decrements. The Autotray is incubated for 18–20 hours at 37° C., at which time the trays are examined visually for growth as evidenced by turbidity, and the concentration of the last sample in the series showing no growth (or no turbidity) is recorded as the minimal inhibitory concentration (MIC). The compounds of formula I were thus found to be antibacterially effective against *Staphylococcus aureus*, *Pseudomonas aeruginosa*, *Escherichia coli*, and *Proteus vulgaris* at concentrations from 2 to 500 mcg./ml.

In standard biological test procedures, the compounds of formula I have also been found to possess antifungal activity, and in particular have been found to be effective against *Ceratocystis ulmi*, the causative agent of Dutch elm disease. The test procedures, the agar growth and shake culture tests, used to determine this latter activity are described as follows: In the agar growth test a solution of 2 mg. of the test compound in 2 ml. of acetone was prepared and 0.2 ml. of this solution was added via sterile glass pipette to 20 ml. of molten (42° C.) sterile potato dextrose agar. Mixing was accomplished by repeated inversion of the tube. The mixture was poured into a sterile Petri dish, allowed to solidify at room temperature, and then was inoculated by placing in the center of the agar-chemical mixturea section (3 mm. diameter) of agar permeated with the mycelium of *Ceratocystis ulmi*. The inoculated dish was incubated at 25° C. for 5 days when the diameter of growth was measured and compared to the growth which had occurred in a control culture. The percent inhibition was calculated as:

$$\% \text{ Inhibition} = \frac{\text{Diameter of untreated} - \text{Diameter of treated}}{\text{Diameter of untreated}} \times 100.$$

In the shake culture test, a 0.2 ml. aliquot of an acetone solution of the test compound (2 mg. in 2 ml.) was added to 20 ml. of sterile potato dextrose broth in a sterile 250 ml. Erlenmeyer flask. The flask was stoppered with a plug of sterile cotton, and the mixture was shaken for one hour on a New Brunswick "gyrotatary" shake table. The mixture was inoculated by addition of a section (3 mm. diameter) of agar permeated with the mycelium of *Ceratocystis ulmi* and returned to the shake table where shaking was continued for five days at room temperature. The optical density of the mixture was measured, using an uninoculated sample of the broth as a blank, and compared with a control sample. The percent inhibition was calculated as:

$$\% \text{ Inhibition} = \frac{100 - \% \text{ transmittance by treated}}{100 - \% \text{ transmittance by untreated}} \times 100.$$

Using the above-described test procedures, the compounds of the invention have been found to have superior activity against *Ceratocystis ulmi* in comparison with the known antifungal agent pyoluteorin, 4,5-dichloropyrrol-2-yl 2,6-dihydroxyphenyl ketone. More specifically, in the agar growth test, the compounds of the invention have been found to be from about three to fourteen times as effective as pyoluteorin, while in the shake culture test, the compounds of the invention have been found to be eitherequally effective or up to about twice as effective as pyoluteorin.

The actual determination of the numerical biological data definitive for a particular compound of formula I is readily determined by standard test procedures by technicians versed in biological test procedures, without the need for any extensive experimentation.

When used as antibacterial agents, the compounds of formula I can be formulated for use by preparing a dilute solution in an organic medium in which the compounds are soluble, for example ethyl alcohol, or in such solution containing a surfactant, and are applied to a surface to be disinfected by conventional methods such as spraying, swabbing, immersion, and the like. Alternatively, the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases such as glycerol and tragacanth. They can also be formulated for use as aerosol sprays or foams.

When used as antifungal agents for treatment of Dutch elm disease, the compounds are formulated for use as emulsifiable concentrates, as wettable powders or flowable pastes, or as true solutions, using in each case, adjuvants of acceptable phytotoxicological character.

In use, the formulations are applied either as a dilute spray to the foliage of the tree at a concentration of from 0.25 to 25 pounds per 100 gallons of water or as an injection into the tree trunk in the form of wettable powders, flowable pastes or solutions containing, in each case, from 5 to 96% active ingredients.

The molecular structures of the compounds of the invention were assigned on the basis of study of their infrared, ultraviolet and NMR spectra, and confirmed by the correspondence between calculated and found values for elemental analyses for the elements.

The following examples will further illustrate the invention without, however, limiting it thereto. All melting points are uncorrected.

EXAMPLE 1

A solution of 6.7 g. (0.1 mole) of pyrrole in 70 ml. of diethyl ether was added slowly and with vigorous stirring to a solution of 20 g. (0.11 mole) of trichloroacetyl chloride in 20 ml. of diethyl ether. When addition was complete, stirring was continued for another half hour, and the solution then treated cautiously with an excess of 10% aqueous potassium carbonate. When frothing had subsided, the organic layer was separated, dried, taken to dryness in vacuo, and the residual solid recrystallized with charcoaling from hexane to give 10.2 g. of pyrrol-2-yl trichloromethyl ketone, m.p. 74°–75° C.

Chlorine was bubbled into 450 ml. of glacial acetic acid until a total of 15.6 g. (0.22 mole) had been taken up. This solution was then added slowly and with vigorous stirring to a solution of 22.3 g. (0.11 mole) of pyrrol-2-yl trichloromethyl ketone in 50 ml. of glacial acetic acid. The mixture was stirred for two hours, concentrated to a small volume, the residue mixed with aqueous potassium carbonate, and extracted with diethyl ether. The combined ether extracts, after drying, charcoaling, and concentration to dryness, afforded a solid residue which was recrystallized from hexane to give 20.2 g. of 4,5-dichloropyrrol-2-yl trichloromethyl ketone, m.p. 129°–131° C.

A mixture of 68 g. (0.24 mole) of 4,5-dichloropyrrol-2-yl trichloromethyl ketone, 115 ml. of 10% aqueous sodium hydroxide and 150 ml. of water was shaken until all solid had dissolved. The mixture was then acidified with concentrated hydrochloric acid, cooled and extracted with diethyl ether. The combined organic extracts were dried over sodium sulfate, charcoaled, concentrated to a volume of about 100 ml., diluted with 200 ml. of hexane, and cooled. The precipitate which separated was collected to give 27.5 g. of 4,5-dichloropyrrole-2-carboxylic acid, m.p. 172°–174° C. A second crop of 6.8 g. of product, m.p. 163°–165° C., was recovered from the filtrate.

A mixture of 18 g. (0.1 mole) of 4,5-dichloropyrrole-2-carboxylic acid and 25 ml. of thionyl chloride was heated on a steam bath for about 20 minutes under reflux until solution was complete and there was not further reaction. The mixture was then concentrated to remove all excess thionyl chloride, the residue diluted with 100 ml. of benzene and the solution added to 13.8 g. (0.10 mole) of 1,3-dimethoxybenzene. The resulting purple solution was stirred and cooled in an ice bath while 26 g. (0.10 mole) of stannic chloride was added in portions over a period of about ten minutes while maintaining the solution at 5°–10° C. The mixture was stirred an additional hour at 5°–10° C., allowed to stand at room temperature for about twelve hours, and poured into 200 ml. of an ice/water mixture. After standing for 2 hours, the solid precipitate was collected and recrystallized, with charcoaling, from diethyl ether to give 12 g. of 4,5-dichloropyrrol-2-yl 2,4-dimethoxyphenyl ketone, m.p. 147°–149° C.

EXAMPLE 2

A solution of 10.7 g. (0.05 mole) of pyrrol-2-yl trichloromethyl ketone (described above in Example 1) was dissolved in 25 ml. of glacial acetic acid, and the solution was treated slowly and with vigorous stirring with a solution of 16 'g. (0.1 mole) of bromine in 25 ml. of glacial acetic acid. When addition was complete, the reaction mixture was warmed at about 50° C. in a water bath for about 15 minutes until the orange bromine color had disappeared. The solution was then concentrated to a small volume, treated cautiously with 10% aqueous potassium carbonate, and the mixture extracted with diethyl ether. The combined ether extracts, on drying and concentration, afforded a solid residue which was recrystallized from hexane to give 15.5 g. of 4,5-dibromopyrrol-2-yl trichloromethyl ketone, m.p. 136°–138° C.

A mixture of 74 g. (0.2 mole) of 4,5-dibromopyrrol-2-yl trichloromethyl ketone in 100 ml. of 10% aqeuous sodium hydroxide and 150 ml. of water was heated and stirred on a steam bath for about ten minutes until all solid had dissolved. The reaction mixture was acidified with concentrated hydrochloric acid, the mixture extracted with diethyl ether, and the combined organic extracts dried, charcoaled, concentrated to a volume of about 100 ml. and diluted with 300 ml. of hexane. The product which separated was collected and dried to give 45 g. of 4,5-dibromopyrrole-2-carboxylic acid, m.p.>160° C. (dec.)

The latter (26.9 g., 0.1 mole) was converted to the corresponding acid chloride by reaction with 25 ml. of thionyl chloride, and the acid chloride reacted with 13.8 g. (0.1 mole) of 1,4-dimethoxybenzene in 100 ml. of benzene in the presence of 26 g. (0.1 mole) of stannic chloride using the procedure described above in Example 1. The product was recrystallized from diethyl ether to give 22.5 g. of 4.5-dibromopyrrol-2-yl 2,5-dimethoxyphenyl ketone, m.p. 166–168° C.

EXAMPLE 3

4,5-Dichloropyrrole-2-carboxylic acid (18.0 g., 0.1 mole) was converted to the corresponding acid chloride by reaction with 25 ml. of thionyl chloride, and the acid chloride dissolved in 100 ml. of benzene was reacted with 13.8 g. (0.1 mole) of 1,2-dimethoxybenzene in the presence of 26 g. (0.1 mole) of stannic chloride using the procedure described above in Example 1. The product was recrystallized from diethyl ether to give 7.9 g. of 4,5-dichloropyrrol-2-yl 3,4-dimethoxyphenyl ketone, m.p. 167°–169° C.

EXAMPLE 4

4,5-Dichloropyrrole-2-carboxylic acid (36.0 g., 0.2 mole) was converted to the corresponding acid chloride by reaction with 50 ml. of thionyl chloride, and the acid chloride dissolved in 200 ml. of benzene was reacted with 27.6 g. (0.2 mole) of 1,4-dimethoxybenzene in the presence of 55 g. (0.2 mole) of stannic chloride using the procedure described above in Example 1. The product was recrystallized from diethyl ether to give two crops totaling 35.5 g. of 4,5-dichloropyrrol-2-yl 2,5-dimethoxyphenyl ketone, m.p. 148°–150° C.

EXAMPLE 5

A solution of 26 g. (0.067 mole) of 4,5-dibromopyrrol-2-yl 2,5-dimethoxyphenyl ketone (described above in Example 2) was treated portionwise with stirring with 26 g. (0.98 mole) of aluminum tribromide, and the mixture was stirred overnight at room temperature. An additional 26 g. (0.98 mole) of aluminum bromide was added, the mixture stirred for two hours at room temperature and then poured into 400 ml. of 3N hydrochloric acid. The mixture was extracted with diethyl ether, the combined extracts were dried over sodium sulfate, charcoaled, diluted with about 300 ml. of benzene and concentrated until a yellow-orange precipitate began to form. The mixture was cooled and the precipitated solid collected and dried to give 17.5 g. of 4,5-dibromopyrrol-2-yl 2,5-dihydroxyphenyl ketone, m.p. 202°–203° C.

EXAMPLE 6

A 57% mineral oil suspension of sodium hydride (21.1 g., 0.5 mole) was washed several times with toluene until free of mineral oil. The sodium hydride was then suspended in 90 ml. of benzene and 10 ml. of dimethylformamide and treated, under nitrogen at 45° C. to 50° C. over a 40 minute period, with 16.75 g. (0.25 mole) of pyrrole in 100 ml. of a 9:1 mixture of benzene/dimethylformamide. The mixture was then treated dropwise at 50° C. to 55° C. over a 70 minute period with 75 g. (0.55 mole) of 4-methoxybenzaldehyde. When addition was complete, the mixture was stirred for an additional 30 minutes, cooled, diluted with water and extracted with diethyl ether. The combined organic extracts were washed three times with water, once with brine, dried over magnesium sulfate, charcoaled, and evaporated to dryness to give 81 g. of a dark oil which was distilled in vacuo at 0.1 mm., all material boiling up to 100 ° C. being discarded. The non-volatile residue was cyrstallized from isopropyl acetate/hexane to give 34.9 g. of pyrrol-2-yl 4-methoxyphenyl ketone, m.p. 106°–109° C.

The latter (10 g., 0.05 mole) was dissolved in 50 ml. of chloroform and 25 ml. of glacial acetic acid and the solution treated with a solution of 16 g. (0.1 mole) of bromine in 25 ml. of glacial acetic acid while maintaining the temperature at 0° C. to −5° C. When addition was complete, the precipitated solid was collected, washed with benzene, and recrystallized from ethanol to give 10.3 g. of 4,5-dibromopyrrol-2-yl 4-methoxyphenyl ketone, m.p. 202°–203° C.

EXAMPLE 7

A solution of 22.7 g. (0.113 mole) of pyrrol-2yl 4-methoxyphenyl ketone (described above in Example 6) in 100 ml. of glacial acetic acid and 50 ml. of carbon tetrachloride was treated with a solution of 16 g. (0.23 mole) of chlorine in 200 ml. of glacial acetic acid using the procedure described above in Example 1. The product which separated from the reaction mixture was collected and recrystallized from benzene to give 9.9 g. of 4,5-dichloropyrrol-2-yl 4-methoxyphenyl ketone, m.p. 186°–188° C.

EXAMPLE 8

Pyrrole (16.75 g., 0.25 mole) was reacted with 21.1 g. (0.5 mole) of a 57% mineral oil suspension of sodium hydride in 100 ml. of a 9:1 solution of benzene/dimethylformamide and the mixture thus obtained reacted with 75 g. (0.5 mole) of 3-methoxybenzaldehyde using the procedure described above in Example 6. The product was purified by distillation in vacuo to give 36.5 g. of pyrrol-2-yl 3-methoxyphenyl ketone, b.p. 131°–133° C./0.02 mm.

The latter (16.7 g., 0.08 mole) dissolved in 100 ml. of glacial acetic acid and 10 ml. of carbon tetrachloride was treated with a solution of 26.6 g. (0.17 mole) of bromine in 50 ml. of glacial acetic acid using the procedure described above in Example 2. The product was recrystallized from isopropanol to give two crops totaling 18.6 g. of 4,5-dibromopyrrol-2-yl 3-methoxyphenyl ketone, m.p. 131°–132° C.

EXAMPLE 9

A solution of 19 g. (0.06 mole) of 4,5-dichloropyrrol 2-yl 2,4-dimethoxyphenyl ketone (described above in Example 1) in 1 liter of benzene was added to a stirred suspension of 100 g. (0.75 mole) of aluminum trichloride in 500 ml. of benzene using the procedure described above in Example 5. The product was recrystallized once from diethyl eiter and once from dilute ethanol to give 6.5 g. of 4,5-dichloropyrrol-2-yl 2,4-dihydroxyphenyl ketone, m.p. 233°–135° C.

EXAPLE 10

To a stirred mixture of 50 g. (0.38 mole) of aluminum trichloride in 500 ml. of benzene was added protionwise over about two minutes 9.0 g. (0.03 mole) of 4,5-dichloropyrrol-2-yl 2,5-dimethoxyphenyl ketone (described above in Example 4) using the procedure described above in Example 5. The product was recrystallized once from diethyl ether, once from xylene and once from dilute ethanol to give 2.7 g. of 4,5-dichloropyrrol-2-yl 2,5-dihydroxyphenyl ketone, m.p. 238°–239° C.

Data obtained for the compounds of the invention in in vitro tests against fungal organism, Ceratocystis ulmi, in the agar growth and shake culture tests in comparison with the known antibiotic, pyoluteorin, at a standard dilution of 10 parts per million are given in terms of percent inhibition in the table below. The compounds are identified by reference to the example number above where their preparation is described.

| Example | % Inhibition Agar Growth | Shake Culture |
| --- | --- | --- |
| 1 | 28 | 30 |
| 2 | 32 | 38 |
| 3 | 25 | 75 |
| 4 | 48 | 72 |
| 5 | 28 | 83 |
| 6 | 11 | 66 |
| 7 | 32 | 61 |
| 8 | 28 | 75 |
| 9 | 55 | 72 |
| 10 | 21 | 64 |
| Pyoluteorin | 4 | 38 |

These results show that at a standard dilution of 10 parts per million in the agar growth test, the compounds of the invention are from about 3 to 14 times as effective as the known pyoluteorin, and in the shake culture test at the same dilution, they are either equally effective or up to about twice as effective as pyoluteorin.

Data, expressed in terms of the minimum inhibitory concentration in mcg./ml., obtained in in vitro tests of the compounds of the invention in comparison with pyoluteorin against the bacterial organisms Staphylococcus aureus 209, Escherichia coli 198, Klebsiella pneumoniae 39645, Proteus vulgaris 9920, and Pseudomonas aeruginosa 211 (identified below as organisms A, B, C, D and E, respectively) are given in the table below.

| Example | Test Organism | | | | |
| --- | --- | --- | --- | --- | --- |
| | A | B | C | D | E |
| 1 | 62.5 | >125 | >125 | >125 | >125 |
| 2 | 31.3 | >125 | >125 | >125 | >125 |
| 3 | >125 | >125 | >125 | >125 | >125 |
| 4 | >125 | >125 | >125 | >125 | >125 |
| 5 | 15.6 | 125 | >125 | 62.5 | 125 |
| 6 | >125 | >125 | >125 | >125 | >125 |
| 7 | >31.6 | 15.6 | >62.5 | 62.5 | >250 |
| 8 | 250 | 250 | >250 | 125 | >125 |
| 9 | 3.9 | 31.3 | >125 | >125 | >125 |
| 10 | 0.98 | 125 | 125 | 62.5 | 125 |
| Pyoluteorin | 3.1 | 6.2 | — | 125 | 125 |

These results show that certain of the species of the invention are from 2 to 3 times as active as the known pyoluteorin against certain microorganisms, i.e. the species of Examples 5 and 7 against Proteus vulgaris 9920 and the species of Example 10 against Staphylococcus aureus 209 and Proteus vulgaris 9920.

I claim:
1. A compound having the formula:

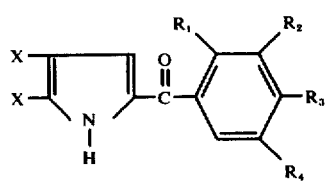

wherein X is chlorine or bromine, both values of X being identical; and two of $R_1$, $R_2$, $R_3$ and $R_4$ are either both hydroxy or both methoxy, the others being hydrogen.

2. A compound according to claim 1 having the formula:

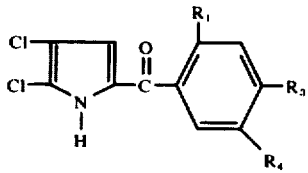

wherein two of $R_1$, $R_3$ and $R_4$ are either both hydroxy or both methoxy, the other being hydrogen.

3. A compound according to claim 1 having the formula:

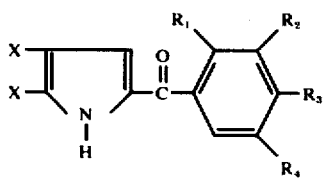

wherein (A) X is chlorine and either two of $R_1$, $R_2$, and $R_3$ and $R_4$ are methoxy, the others being hydrogen or $R_1$ and $R_3$ are each hydroxy and $R_2$ and $R_4$ are hydrogen and (B) X is bromine and $R_1$ and $R_4$ are each hydroxy and $R_2$ and $R_3$ are hydrogen.

4. A compound according to claim 1 wherein two of $R_1$, $R_2$, $R_3$ and $R_4$ are hydroxy.

5. A compound according to claim 1 wherein two of $R_1$, $R_2$, $R_3$ and $R_4$ are methoxy.

6. 4,5-Dichloropyrrol-2-yl 2,4-dihydroxyphenyl ketone according to claim 2.

7. 4,5-Dichloropyrrol-2-yl 2,5-dimethoxyphenyl ketone according to claim 2.

8. 4,5-Dibromopyrrol-2-yl 2,5-dihydroxyphenyl ketone according to claim 3.

9. 4,5-Dichloropyrrol-2-yl 3,4-dimethoxyphenyl ketone according to claim 3.

10. 4,5-Dichloropyrrol-2-yl 2,5-dihydroxyphenyl ketone according to claim 2.

11. 4,5-Dichloropyrrol-2-yl 2,4-dimethoxyphenyl ketone according to claim 5.

12. 4,5-Dibromopyrrol-2-yl 2,5-dimethoxyphenyl ketone according to claim 5.

* * * * *

UNITED STATES PATENT AND TRADEMARK OFFICE
CERTIFICATE OF CORRECTION

PATENT NO. : 4,000,160
DATED : December 28, 1976
INVENTOR(S) : Denis M. Bailey

It is certified that error appears in the above-identified patent and that said Letters Patent are hereby corrected as shown below:

Column 1, line 30 "4,5-di-X-pyrrl-2-yl 2-$R_1$-3-$R_2$-4-$R_4$-phenyl ketones" should read --4,5-di-X-pyrrol-2-yl 2-$R_1$-3-$R_2$-4-$R_3$-5-$R_4$-phenyl ketones--.

Column 5, line 14 reads "...mixturea section..." and should read --...mixture a section...--

Column 5, lines 28-29 reads "...New Brunswick "gyrotatary" shake table..." and should read --New Brunswick "Gyrotary" shake table...--.

Column 5, line 51 "eitherequally" should read --either equally--.

Signed and Sealed this

Twelfth Day of December 1978

[SEAL]

Attest:

RUTH C. MASON
Attesting Officer

DONALD W. BANNER
Commissioner of Patents and Trademarks